United States Patent
Wang et al.

(10) Patent No.: US 11,463,676 B2
(45) Date of Patent: Oct. 4, 2022

(54) STEREOSCOPIC VISUALIZATION SYSTEM AND METHOD FOR ENDOSCOPE USING SHAPE-FROM-SHADING ALGORITHM

(71) Applicant: MING SHI CO., LTD., Changhua (TW)

(72) Inventors: Yen-Yu Wang, Caotun Township, Nantou County (TW); Kai-Che Liu, Kaohsiung (TW); Atul Kumar, Lukang Township, Changhua County (TW); Min-Liang Wang, Taichung (TW)

(73) Assignee: MEDICALTEK CO. LTD., Taichung (TW)

( * ) Notice: Subject to any disclaimer, the term of this patent is extended or adjusted under 35 U.S.C. 154(b) by 386 days.

(21) Appl. No.: 16/822,823

(22) Filed: Mar. 18, 2020

(65) Prior Publication Data
US 2020/0221069 A1 Jul. 9, 2020

Related U.S. Application Data

(63) Continuation-in-part of application No. 14/821,042, filed on Aug. 7, 2015, now abandoned.

(51) Int. Cl.
*H04N 13/268* (2018.01)
*H04N 13/156* (2018.01)
(Continued)

(52) U.S. Cl.
CPC ....... *H04N 13/268* (2018.05); *A61B 1/00045* (2013.01); *A61B 1/00193* (2013.01);
(Continued)

(58) Field of Classification Search
CPC .. H04N 13/156; H04N 13/261; H04N 13/268; H04N 5/2256; G06T 7/70; G06T 7/507
See application file for complete search history.

(56) References Cited

U.S. PATENT DOCUMENTS

| 8,488,868 B2 * | 7/2013 | Tam ................. H04N 13/257 348/44 |
| 2008/0031327 A1 | 2/2008 | Wang et al. |

(Continued)

OTHER PUBLICATIONS

Kuumar et al., "Stereoscopic visualization of laparoscope image using depth information from 3D model," Computer Methods and Programs in Biomedicine, vol. 113, Issue 3, 2014, pp. 862-868, 7 pages.

(Continued)

*Primary Examiner* — Brian P Yenke
(74) *Attorney, Agent, or Firm* — Muncy, Geissler, Olds & Lowe, P.C.

(57) ABSTRACT

A stereoscopic visualization system using shape from shading algorithm is an image conversion device connected between a monoscopic endoscope and a 3D monitor. The system applies the algorithm which generates a depth map for a 2D image of video frames. The algorithm first calculates a direction of a light source for the 2D image. Based upon the information of light distribution and shading for the 2D image, the depth map is generated. The depth map is used to calculate another view of the original 2D image by depth image based rendering algorithm in generation of stereoscopic images. After the new view is rendered, the stereoscopic visualization system also needs to convert the display format of the stereoscopic images for different kinds of 3D displays. Based on this method, it can replace the whole monoscopic endoscope with a stereo-endoscope system and no modification is required for the monoscopic endoscope.

5 Claims, 2 Drawing Sheets

(51) Int. Cl.
*H04N 13/261* (2018.01)
*H04N 5/225* (2006.01)
*G06T 7/507* (2017.01)
*G06T 7/70* (2017.01)
*A61B 1/00* (2006.01)

(52) U.S. Cl.
CPC ............... *G06T 7/507* (2017.01); *G06T 7/70* (2017.01); *H04N 5/2256* (2013.01); *H04N 13/156* (2018.05); *H04N 13/261* (2018.05); *G06T 2207/10068* (2013.01); *G06T 2207/20212* (2013.01); *H04N 2005/2255* (2013.01)

(56) References Cited

U.S. PATENT DOCUMENTS

| | | | |
|---|---|---|---|
| 2010/0182406 A1* | 7/2010 | Benitez | G06T 7/55 348/46 |
| 2011/0084966 A1* | 4/2011 | Kao | G09G 3/3611 345/426 |
| 2011/0304708 A1* | 12/2011 | Ignatov | H04N 13/128 348/51 |
| 2013/0147911 A1 | 6/2013 | Karsch et al. | |
| 2013/0345509 A1 | 12/2013 | Alamaro et al. | |
| 2014/0198976 A1 | 6/2014 | Coffman | |
| 2014/0243596 A1* | 8/2014 | Yoon | A61B 1/00009 600/111 |
| 2015/0237325 A1* | 8/2015 | Angot | G06T 7/579 348/47 |
| 2016/0295194 A1* | 10/2016 | Wang | A61B 1/00194 |
| 2017/0035268 A1* | 2/2017 | Kumar | A61B 1/00009 |
| 2019/0051039 A1* | 2/2019 | Tsuru | G06T 15/506 |
| 2019/0132579 A1* | 5/2019 | Springer | G02B 27/08 |
| 2020/0221069 A1* | 7/2020 | Wang | G06T 7/70 |

OTHER PUBLICATIONS

Sanko et al., Image Processing, Analysis and Machine Vision, 2000, http://user.engineering.uiowa.edu/~dip/LECTURE/lecture.html, Chapter 9.

Stoyanov et al., "Illumination position estimation for 3D soft tissue reconstruction in robotic minimally invasive surgery," 2009, IEEE/RSJ International Conference on Intelligent Robots and System (IROS).

Visentini-Scarzanella et al., "Metric depth recovery from monocular images using Shape-from-Shading and specularities," 2012, 19$^{th}$ IEEE International Conference on Image Processing, pp. 25-28, 4 pages.

* cited by examiner

STEREOSCOPIC VISUALIZATION SYSTEM AND METHOD FOR ENDOSCOPE USING SHAPE-FROM-SHADING ALGORITHM

CROSS-REFERENCE TO RELATED APPLICATION

This application is a continuation in part of U.S. patent application Ser. No. 14/821,042, filed on Aug. 7, 2015, in the United States Patent and Trademark Office, the content of which is incorporated herein in its entirety by reference.

BACKGROUND OF THE INVENTION

1. Field of the Invention

The present invention relates to a stereoscopic visualization system for endoscope and, more particularly, to a stereoscopic visualization system for endoscope using shape-from-shading algorithm to generate stereo images.

2. Description of the Related Art

Minimally invasive surgery has become an indispensable part in surgical treatment of current medical behavior and can be performed by endoscope-assisted surgical instruments to allow smaller incision and less tissue trauma, thereby shortening patient's recovery cycle and reducing overall medical expense. However, conventional minimally invasive surgery all employs monoscopic endoscope, which only displays two-dimensional (2D) images lacking depth information. Therefore, it is challenging for a surgeon to accurately move surgical instruments to a correct location inside a patient's body. Surgeons usually perceive depth in 2D images according to motion parallax, monocular cues and other indirect evidences for positioning accuracy. Providing stereo images capable of directly providing depth perception without going through additional means, such as motion parallax, monocular cues and other indirect evidences, is still the best approach in resolving the conventional inaccurate positioning issue at the cost of a dual-camera endoscope, such as US-A-2014/198976, which provides a stochastic method and system for fast stereoscopic ranging includes selecting a pair of images for stereo processing, in which the pair of images are a frame pair and one of the image is a reference frame. Despite the advantages of depth information or stereo images required by surgeons, the dual-camera endoscope has the drawback of being much more expensive than the monoscopic endoscope and is less accepted accordingly.

SUMMARY OF THE INVENTION

An objective of the present invention is to provide a stereoscopic visualization system and a stereoscopic visualization method using shape-from-shading algorithm capable of providing stereoscopic images with a monoscopic endoscope through the shape-from-shading algorithm.

To achieve the foregoing objective, the stereoscopic visualization system for endoscope using shape-from-shading algorithm includes a monoscopic endoscope, a three-dimensional (3D) display, and an image conversion device.

The monoscopic endoscope may capture the two-dimensional (2D) images.

The image conversion device may be connected between the monoscopic endoscope and the 3D display and may have an input port for endoscope and a 2D-to-3D conversion unit.

The input port for endoscope may be connected to the monoscopic endoscope to receive the 2D image from the monoscopic endoscope.

The 2D-to-3D conversion unit may apply shape from shading algorithm adapted to calculate a direction of a light source for the 2D image, and may calculate a depth map based upon information of light distribution and shading of the 2D image, illumination position estimation being added to form a pixel information of each pixel in the 2D image and the pixel information comprising a pixel intensity value, an illumination direction and a natural logarithm of coordinates of the pixel, and using the depth map to create a disparity map and may apply depth image based rendering algorithm to convert the 2D image to a stereoscopic image with a left image and a right image generated from the disparity map.

The image output port may be connected with the 2D-to-3D image conversion unit and the 3D display to receive the stereo images and display the stereo image on the 3D display.

A reflected highlight part of the 2D image may be removed to form a reference image and the depth map may be improved by combining the reference image and the depth map. The depth map is composed of a gray-level image containing information relating to a distance of scene objects on the 2D image from a viewpoint, and disparity values in the disparity map are inversely proportional to corresponding pixel intensity values of the depth maps and are proportional to a focal length of the camera of the monoscopic endoscope and an interorbital width of a viewer.

The reflected highlight part of the 2D image may be removed without removing edges and lines of the 2D image.

To achieve the foregoing objective, the stereoscopic visualization method for endoscope using shape-from-shading algorithm includes steps of: capturing a two-dimensional (2D) image, wherein an image-capturing unit is used to acquire a 2D image from a monoscopic endoscope with illumination from a light source;

reducing a highlight part of the 2D image and forming a reference image;

generating a depth map of the 2D image using the shape-from-shading method, wherein the shape-from-shading method combines a light direction and an iterative approach to solve equations involving a gradient variation of pixel intensity values in the 2D image and illumination position estimation is added to form a pixel information of each pixel in the 2D image and the pixel information comprises a pixel intensity value, an illumination direction and a natural logarithm of coordinates of the pixel;

improving the depth map by combining the reference image and the depth map;

creating a disparity map using the depth map, the depth map being composed of a gray-level image containing information relating to a distance of scene objects on the 2D image from a viewpoint, wherein disparity values in the disparity map are inversely proportional to corresponding pixel intensity values of the depth maps and are proportional to a focal length of the camera of the monoscopic endoscope and an interorbital width of a viewer; and generating a stereoscopic image by combining the depth map and the 2D image.

Given the foregoing stereoscopic visualization system and method using shape-from-shading method, the 2D image taken by the monoscopic endoscope is processed by the shape-from-shading algorithm to calculate depth information in generation of a depth map, and the 2D image along with the depth map form the stereoscopic image that is outputted to the 3D display for users to view the converted stereoscopic image. As there is no need to replace a monoscopic endoscope with a dual-lens endoscope and modify the hardware structure of the existing monoscopic endoscope, the issues of no stereoscopic image available to monoscopic endoscope and costly dual-lens endoscope encountered upon the demand of stereoscopic images can be resolved.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
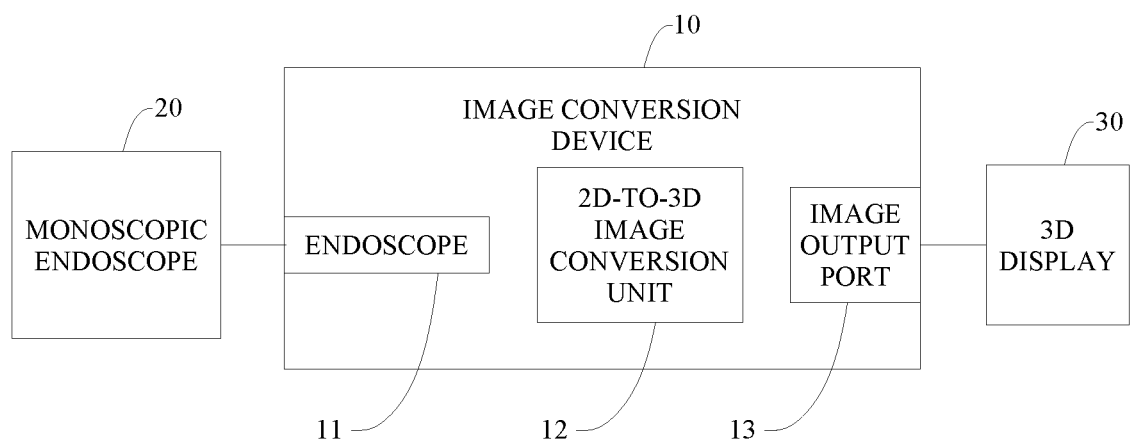
FIG. 1 is a functional block diagram of a stereoscopic visualization system for endoscope using shape-from-shading algorithm in accordance with the present invention.

With reference to FIG. 1, a stereoscopic visualization system for endoscope using shape-from-shading algorithm in accordance with the present invention includes a monoscopic endoscope 20, a three-dimensional (3D) display 30, and an image conversion device 10.

The image conversion device 10 is connected between the monoscopic endoscope 20 and the 3D display 30, and has an input port for endoscope 11, a 2D-to-3D image conversion unit 12, and an image output port 13. The input port for endoscope 11 is connected to the monoscopic endoscope 20. The 2D-to-3D image conversion unit 12 is electrically connected to the input port for endoscope 11, acquires a 2D image from the monoscopic endoscope 20, generates a depth map of the 2D image, and converts the 2D images and the depth map into a stereoscopic image using shape-from-shading algorithm built in the 2D-to-3D image conversion unit 12. The image output port 13 is electrically connected to the 2D-to-3D image conversion unit 12, and also connected to the 3D display 30, and outputs the stereoscopic image to the 3D display 30 such that the 3D display 30 displays the converted stereoscopic images.

Figure 2:
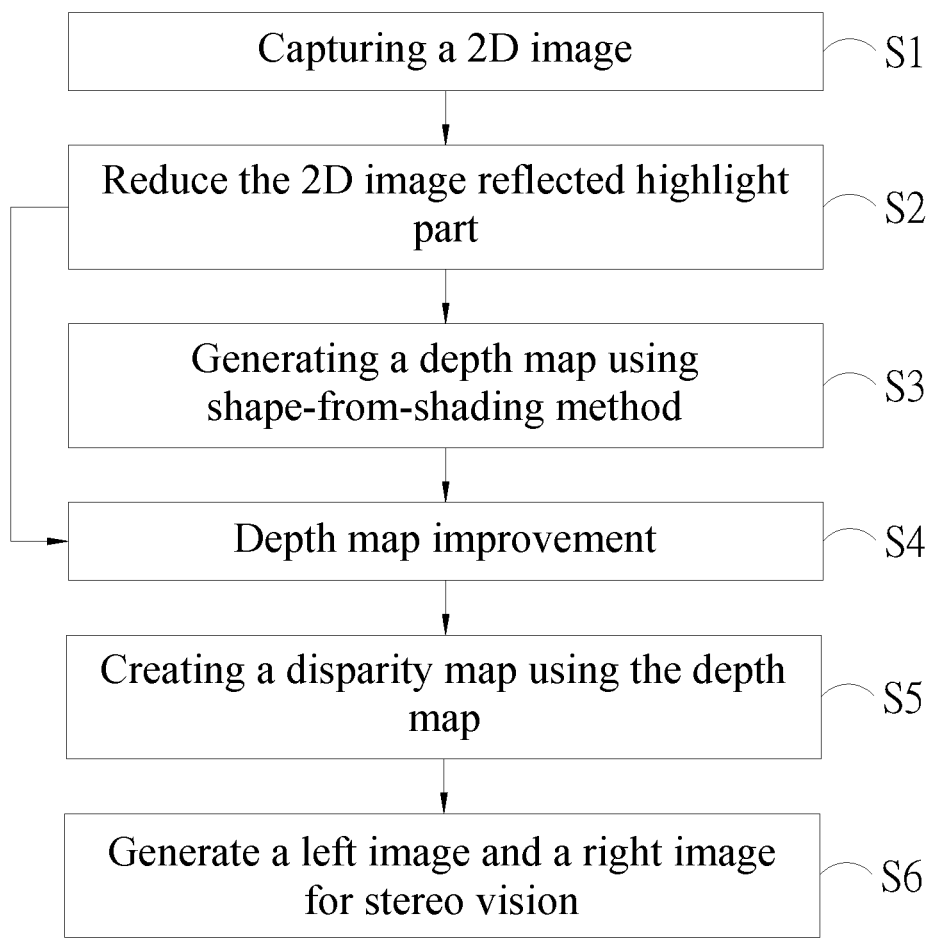
FIG. 2 is a flow diagram of a stereoscopic visualization method for endoscope using shape-from-shading algorithm in accordance with the present invention.

With reference to FIG. 2, a stereoscopic visualization method for endoscope using shape-from-shading algorithm in accordance with the present invention is performed by the 2D-to-3D image conversion unit 12 to convert the 2D images from the monoscopic endoscope 20 into the stereoscopic images, and includes the following steps.

Step S1: Capturing a 2D image. An image-capturing device is used to acquire a 2D image from the camera of the monoscopic endoscope. The image-capturing device may have a resolution being standard definition (SD) or high definition (HD). The camera of the monoscopic endoscope may have a 30 degree lens or a wide angle lens.

Step S2: Reduce the 2D image reflected highlight part. The 2D image with highlight part will make peak value, that show the wrong part of rendering gradient on depth map by shape from shading method. In this step, try to remove the highlight part in capture 2D image, so as to form a reference image.

Step S3: Generating a depth map using shape-from-shading method. With reference to "Metric depth recovery from monocular images using shape-from-shading and specularities, Visentini-Scarzanella et al. 2012 IEEE Internal Conference on Image Processing", a shape-from-shading algorithm is employed to calculate lighting information and shading information of the 2D image generated from a light source. Then use an iterative approach to solve equations involving gradient variation of pixel information in the 2D image, and combine information associated with an illumination direction and a position of the light source to calculate a depth map of the pixels in the 2D image relative to the light source. An illumination position estimation of the light source disclosed in "Danail Stoyanov et al., 2009 IEEE/RSJ International Conference on Intelligent Robots and System (IROS), Illumination position estimation for 3D soft tissue reconstruction in robotic minimally invasive surgery" is provided to enhance accuracy in determining position of a light source. The pixel information of each pixel in the 2D image includes a pixel intensity value, the illumination direction and the natural logarithm of coordinates of the pixel. Fast sweeping methods disclosed in "Chiu-Yen Kao et al. SIAM J., Numerical Analysis 2005, Fast sweeping methods for static Hamilton-Jacobi equation" and parallel computation can be applied to speed up the iterative process.

The depth map of the image caused by light distribution can thus be generated after iterations of calculation. As being almost the same, the light vector and the camera position vector can be simplified to be the same vector.

Step S4: Depth map improvement. The depth map by shape from shading method is not sharp enough to render stereo images. The smooth depth makes stereo vision with more image distortion issue. In this step, combine the reference image from the step S2 (the capture image reduces the reflection area) and the initial depth map (result from shape from shading method). The reference image provides the edge of image content and the depth map give depth information.

The reference image from the step S2 can be further processed with a denoise filter. There is a technique to reduce image noise without removing significant part of the image content. Typically edges, lines or other detail that are important of the image.

Step S5: Creating a disparity map using the depth map. The depth map is composed of a gray-level image containing information relating to the distance of scene objects on the 2D image from a viewpoint. During the course of converting the depth map into a 3D stereo image pair, a disparity map is generated. Disparity values in the disparity map are inversely proportional to the corresponding pixel intensity values of the depth maps but are proportional to a focal length of a camera of the monoscopic endoscope and an interorbital width of a viewer.

Step S6: Generate a left image and a right image for stereo vision. The disparity map acquired during the course of converting the depth map into the 3D stereo image pair is used for generation of a left eye image and a right eye image. Each disparity value of the disparity map represents a distance between two corresponding points in the left eye image and the right eye image for generation of the left eye image and the right eye image associated with the 3D stereo image pair. The generated left eye image and right eye image can be further processed for various 3D display formats, such as side-by-side, interlaced and other 3D display formats, for corresponding 3D displays to display.

As can be seen from the foregoing description, the depth information can be calculated from the 2D image by using the shape-from-shading algorithm. After generation of the depth map, the 2D images can be combined with the depth maps to generate corresponding stereoscopic images without either replacing the conventional monoscopic endoscope with a dual-lens endoscope or altering the hardware structure of the conventional monoscopic endoscope. Accordingly, the issues arising from the conventional monoscopic endoscope providing no 3D stereo images and the costly dual-lens endoscope can be resolved.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A stereoscopic visualization system for endoscope using shape-from-shading algorithm, comprising:
   a monoscopic endoscope capturing two-dimensional (2D) image;
   a three-dimensional (3D) display; and
   an image conversion device connected between the monoscopic endoscope and the 3D display, and having:
      an input port for endoscope connected to the monoscopic endoscope to receive the 2D image from the monoscopic endoscope;
      a 2D-to-3D conversion unit applying shape from shading algorithm adapted to calculate a direction of a light source for the 2D image, and calculating a depth map based upon information of light distribution and shading of the 2D image, illumination position estimation being added to form a pixel information of each pixel in the 2D image and the pixel information comprising a pixel intensity value, an illumination direction and a natural logarithm of coordinates of the pixel, and using the depth map to create a disparity map and applying depth image based rendering algorithm to convert the 2D image to a stereoscopic image with a left image and a right image generated from the disparity map; and
      an image output port connected with the 2D-to-3D image conversion unit and the 3D display to receive the left image and the right image and display the stereoscopic image on the 3D display;
   wherein a reflected highlight part of the 2D image is removed to form a reference image and the depth map is improved by combining the reference image and the depth map;
   wherein the depth map is composed of a gray-level image containing information relating to a distance of scene objects on the 2D image from a viewpoint, wherein disparity values in the disparity map are inversely proportional to corresponding pixel intensity values of the depth maps and are proportional to a focal length of the camera of the monoscopic endoscope and an interorbital width of a viewer.

2. The stereoscopic visualization system as claimed in claim 1, wherein the reflected highlight part of the 2D image is removed without removing edges and lines of the 2D image.

3. A stereo display method for endoscope using shape-from-shading algorithm, comprising steps of:
   capturing a two-dimensional (2D) image, wherein an image-capturing unit is used to acquire a 2D image from a monoscopic endoscope with illumination from a light source;
   reducing a highlight part of the 2D image and forming a reference image;
   generating a depth map of the 2D image using shape-from-shading method, wherein the shape-from-shading method combines a light direction and an iterative approach to solve equations involving a gradient variation of pixel intensity values in the 2D image, wherein illumination position estimation is added to form a pixel information of each pixel in the 2D image and the pixel information comprises a pixel intensity value, an illumination direction and a natural logarithm of coordinates of the pixel;
   improving the depth map by combining the reference image and the depth map;
   creating a disparity map using the depth map, the depth map being composed of a gray-level image containing information relating to a distance of scene objects on the 2D image from a viewpoint, wherein disparity values in the disparity map are inversely proportional to corresponding pixel intensity values of the depth maps and are proportional to a focal length of the camera of the monoscopic endoscope and an interorbital width of a viewer; and
   generating a stereoscopic image by using the disparity map for generating a left image and a right image, and displaying the left image and the right image by a 3D display.

4. The stereo display method as claimed in claim 3, wherein the reflected highlight part of the 2D image is removed without removing edges and lines of the 2D image.

5. The stereo display method as claimed in claim 3, wherein the stereoscopic image is generated according to the depth image based rendering algorithm to provide different views of the 2D image with the 2D image and the depth map.

* * * * *